United States Patent [19]
Winter et al.

[11] Patent Number: 5,869,584
[45] Date of Patent: Feb. 9, 1999

[54] PROCESS FOR THE PREPARATION OF AN OLEFIN POLYMER USING METALLOCENES CONTAINING SPECIFICALLY SUBSTITUTED INDENYL LIGANDS

[75] Inventors: Andreas Winter, Glashuetten; Frank Kueber, Oberursel; Walter Spaleck, Liederbach; Herbert Riepl, Dachau; Wolfgang Anton Herrmann, Freising; Volker Dolle, Bensheim; Juergen Rohrmann, Kelkheim, all of Germany

[73] Assignee: Targor GmbH, Germany

[21] Appl. No.: 458,428

[22] Filed: Jun. 2, 1995

Related U.S. Application Data

[62] Division of Ser. No. 101,408, Aug. 3, 1993, Pat. No. 5,455,365.

[30] Foreign Application Priority Data

Aug. 3, 1992 [DE] Germany .......................... 42 25 649.6

[51] Int. Cl.$^6$ .............. C08F 4/602; C08F 10/00
[52] U.S. Cl. .......... 526/127; 525/268; 526/121; 526/122; 526/134; 526/160; 526/351
[58] Field of Search .................. 526/127, 160, 526/121, 122, 170

[56] References Cited

U.S. PATENT DOCUMENTS

| | | |
|---|---|---|
| 4,769,510 | 9/1988 | Kaminsky et al. . |
| 4,794,096 | 12/1988 | Ewen ........................ 526/160 |
| 4,892,851 | 1/1990 | Ewen et al. . |
| 4,931,417 | 6/1990 | Miya et al. . |
| 5,004,820 | 4/1991 | Buchwald et al. . |
| 5,087,677 | 2/1992 | Brekner et al. . |
| 5,103,030 | 4/1992 | Rohrmann et al. . |
| 5,120,867 | 6/1992 | Welborn, Jr. . |
| 5,145,819 | 9/1992 | Winter et al. . |
| 5,243,001 | 9/1993 | Winter et al. ............ 526/127 |
| 5,276,208 | 1/1994 | Winter et al. ............ 526/129 |
| 5,296,434 | 3/1994 | Karl et al. ................ 502/117 |
| 5,324,800 | 6/1994 | Welborn, Jr. ............ 526/160 |
| 5,329,031 | 7/1994 | Miyake et al. . |
| 5,329,033 | 7/1994 | Spaleck et al. ............ 556/53 |
| 5,374,752 | 12/1994 | Winter et al. . |

FOREIGN PATENT DOCUMENTS

| | | |
|---|---|---|
| 0 129 368 | 12/1984 | European Pat. Off. . |
| 0 185 918 | 7/1985 | European Pat. Off. . |
| 0 316 155 | 5/1989 | European Pat. Off. . |
| 0 320 762 | 6/1989 | European Pat. Off. . |
| 0 336 128 | 10/1989 | European Pat. Off. . |
| 0 344 887 | 12/1989 | European Pat. Off. . |
| 0 351 392 | 1/1990 | European Pat. Off. . |
| 0 355 289 | 2/1990 | European Pat. Off. . |
| 0 366 290 | 5/1990 | European Pat. Off. . |
| 0 407 870 | 1/1991 | European Pat. Off. . |
| 0 426 643 | 5/1991 | European Pat. Off. . |
| 0 433 990 | 6/1991 | European Pat. Off. . |
| 442 725 | 8/1991 | European Pat. Off. . |
| 442725 | 8/1991 | European Pat. Off. . |
| 0 485 821 | 5/1992 | European Pat. Off. . |
| 0 485 823 | 5/1992 | European Pat. Off. . |
| 0 500 005 | 8/1992 | European Pat. Off. . |
| 0 529 908 | 3/1993 | European Pat. Off. . |
| 0 530 908 | 3/1993 | European Pat. Off. . |
| 529908 | 3/1993 | European Pat. Off. . |
| 37 26 067 | 2/1989 | Germany . |
| 4 035 886 | 11/1990 | Germany . |
| 4 128 238 | 8/1991 | Germany . |

OTHER PUBLICATIONS

Spaleck et al., New J. Chem., "*Stereorigid Metallocenes: Correlations Between Structure and Behaviour in Homopolymerizations of Propylene*", vol. 14, pp. 499–403 (1990).

Röll, V.W., et al., Angew. Chem., "*Stereo– und Regioselektivatat von chiralen, alkylsubstituierten ansa–Zirconocen-–Katalysatoren bei der Methylalumoxan–aktivierten Propen–Polymerization*", vol. 102, No. 3, pp. 339–341 (1990).

Piccoliovazzi, N. et al., Organometallics, "*Electronic Effects in Homogeneous Indenylzirconium Ziegler–Natta Catalysts*", vol. 9, pp. 3098–3105 (1990).

Miyamota, T.K., et al., Chemistry Letters, The Chemical Society of Japan, "*a Bulky Ligand and its Organometallic Compound: Synthesis of Heptamethylidene and a Ferrocene–Type Complex, Fe($n^5$–$C_9Me_7$)$_2$*", pp. 729–730 (1981).

Esperas, S., Acta Chemica Scandinavica, "*The Crystal and Molecular Structure of Cyano(methylisocyanide)gold(I)*", A 30, No. 7, pp. 527–530 (1976).

Adcock et al., Austr. J. Chem., vol. 29, "Substituent Effects by $^{19}$F Nuclear Magnetic Resonance: Polar and π–Electron Effects", pp. 2571–2581.

(List continued on next page.)

*Primary Examiner*—Edward J. Smith
*Attorney, Agent, or Firm*—Connolly & Hutz

[57] ABSTRACT

A highly effective catalyst system for the polymerization of olefins comprises a cocatalyst, preferably an aluminoxane, and a metallocene of the formula I

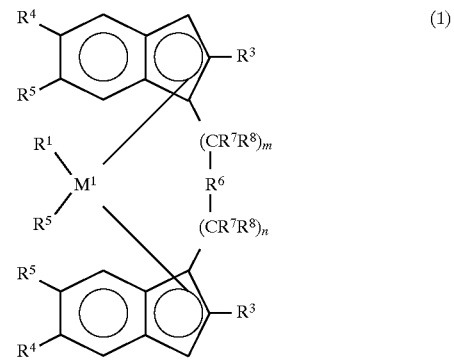

(1)

in which, preferably $M^1$ is Zr or Hf, $R^1$ and $R^2$ are alkyl or halogen, $R^5$ is hydrogen or alkyl, $R^3$ and $R^4$ are alkyl, where $R^3$, $R^4$ and $R^5$ may be halogenated, —$(CR^7R^8)_m$—$R^6$—$(CR^7R^8)_n$— is a single- or multi-membered chain in which $R^6$ may also be a (substituted) heteroatom, and m+n is zero or 1.

12 Claims, No Drawings

OTHER PUBLICATIONS

Marechal et al., *Bull. Soc. Chim. Fr. 6,* "Homopolymerisation cationlique des dimethyl–4,7,dimethyl–4,6 et dimethyl–5,6 indenes", No. 348, pp. 1981–2039, (1969). Chemical Abstracts 90:567 103691p; (1978).

Criegee et al., *Chem. Ber.,* vol. 94, "Uber den Nickelkomplex $C_{18}H_{22}Ni$ und den daraus gewonnenen Kohlenwasserstoff $C_{13}H_{18}$", pp. 3461–3468 (1964).

Hart et al., Notes, *J. Am. Chem. Soc.,* vol. 72, "Acylation–Alkylation Studies", pp. 3286–3287 (1950).

Katz, Thomas J., *J. Am. Chem. Soc.,* "Asymmetric Synthesis of Helical Metallocenes", vol. 108, 1986, pp. 179–181.

Ewen, J.A., et al, *J. Am. Chem. Soc.,* Crystal Structures and Sterospecific Propylene Polymerizations with Chiral Hafnium Metallocene Catalysts, vol. 109, 1987, pp. 6544–6545.

Bulletin de la Societe Chimique de France, "*Etude de monomeres halogenes et de leur polymerisation cationique*", No. 11, pp. 3092–3095, (1973).

J. Org. Chem., "*Friedel–Crafts Reactions of Ethyl Cyclopropanecarboxylate*", vol. 46, pp. 3758–3760 (1981).

Soga, K. et al., Macromolecules, "*Perfect Conversion of Aspecific Sites into Isopecific Sites in Ziegler–Natta Catalysts*", vol. 22, pp. 3824–3826 (1989).

J. Org. Chem., "*Friedel–Crafts Chemistry. A Mechanistic Study of the Reaction of 3–Chloro–4'–fluoro–2–methylpropiophenone with $AlCl_3$ and $AlCl_3$–$CH_3NO_2$*", vol. 43, No. 16, pp. 3126–3131 (1978).

Chemical Abstracts, vol. 117, 1992, Lee et al., *Electronic Effects of Ziegler–Natta Polymerization of Propylene and Ethylene Using Soluble Metallocene Catalysts.*

Journal of the American Chemical Society, Bd. 115, Jul. 14, 1993, J.R. Hart, *Predicted Structure Selectivity Trends: Propylene Polymerization with Substituted RAC–(1, 2–Ethylenebis(.ETA.5–Indenyl)Zirconium (IV) Catalysts.*

PROCESS FOR THE PREPARATION OF AN OLEFIN POLYMER USING METALLOCENES CONTAINING SPECIFICALLY SUBSTITUTED INDENYL LIGANDS

This application is a divisional of application Ser. No. 08/101,408 filed Aug. 3, 1993 now U.S. Pat. No. 5,455,365.

The invention relates to a process for the preparation of olefin polymers and copolymers using metallocenes containing specifically substituted indenyl ligands.

The use of chiral metallocenes as a catalyst component in the polymerization of olefins is known and gives highly isotactic polyolefins of high crystallinity and high melting point (cf. Angew. Chem. 97 (1985) 507, German Patent 40 35 886.0).

If achiral metallocenes are used, atactic polymers are obtained which, due to their unbalanced and inadequate product properties, are only of restricted industrial importance.

Of considerable interest are products whose property profile is between these two extremes.

The object was to find a suitable process or a suitable catalyst system which enables the preparation of polymers of reduced crystallinity, increased impact strength, increased transparency, good flow properties at the processing temperature, reduced melting point and high molecular weight.

The main applications of such polymers are plasticizer and lubricant formulations, hot-melt adhesive applications, coatings, seals, insulations, slush-molding compositions or sound-insulation materials.

The invention thus relates to a process for the preparation of an olefin polymer by polymerization or copolymerization of an olefin of the formula $R^a$—CH=CH—$R^b$, in which $R^a$ and $R^b$ are identical or different and are a hydrogen atom or a hydrocarbon radical having 1 to 14 carbon atoms, or $R^a$ and $R^b$, together with the atoms connecting them, can form a ring, at a temperature of from –60° to 200° C., at a pressure of from 0.5 to 100 bar, in solution, in suspension or in the gas phase, in the presence of a catalyst formed from a metallocene as transition-metal compound and a cocatalyst, wherein the metallocene is a compound of the formula I

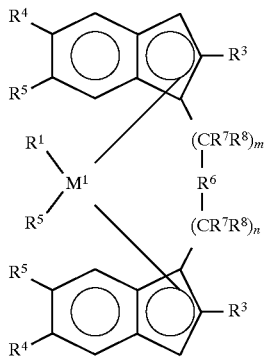

(1)

in which $M^1$ is a metal from group IVb, Vb or VIb of the Periodic Table, $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom, $R^3$, $R^4$ and $R^5$ are identical or different and $R^3$ and $R^4$ and/or $R^5$ are other than hydrogen and are a $C_1$–$C_{20}$-alkyl group, a $C_6$–$C_{20}$-aryl group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, it also being possible for these radicals to be halogenated, $R^4$ or $R^5$ may alternatively be hydrogen, $R^6$ is

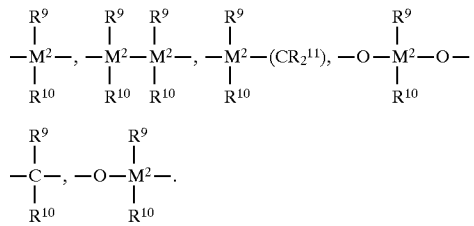

=$BR^9$, =$AlR^9$, —Ge—, —Sn—, —O—, —S—, =SO, =$SO_2$, =$NR^9$, =CO, =$PR^9$ or =$P(O)R^9$, where $R^9$, $R^{10}$ and $R^{11}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^9$ and $R^{10}$ or $R^9$ and $R^{11}$, in each case together with the atoms connecting them, form a ring, $M^2$ is silicon, germanium or tin, $R^7$ and $R^8$ are identical or different and are as defined for $R^9$, and m and n are identical or different and are zero, 1 or 2, where m plus n is zero, 1 or 2.

Alkyl is straight-chain or branched alkyl. Halogen, (halogenated) denotes fluorine, chlorine, bromine or iodine, preferably fluorine or chlorine.

The indenyl ligands of the metallocene of the formula I used in the process according to the invention are substituted in the 2-position ($R^3$) and in at least one of the two positions 5 ($R^4$) and 6 ($R^5$).

The catalyst to be used for the process according to the invention comprises a cocatalyst and a metallocene of the formula I.

In the formula I, $M^1$ is a metal from group IVb, Vb or VIb of the Periodic Table, for example titanium, zirconium, hafnium, vanadium, niobium, tantalum, chromium, molybdenum or tungsten, preferably zirconium, hafnium or titanium.

$R^1$ and $R^2$ are identical or different and are a hydrogen atom, a $C_1$–$C_{10}$-, preferably $C_1$–$C_3$-alkyl group, a $C_1$–$C_{10}$-, preferably $C_1$–$C_3$-alkoxy group, a $C_6$–$C_{10}$-, preferably $C_6$–$C_8$-aryl group, a $C_6$–$C_{10}$-, preferably $C_6$–$C_8$-aryloxy group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$-, preferably $C_7$–$C_{12}$-alkylaryl group, a $C_8$–$C_{40}$-, preferably $C_8$–$C_{12}$-aryl-alkenyl group or a halogen atom, preferably chlorine.

$R^3$, $R^4$ and $R^5$ are identical or different and $R^3$ and $R^4$ and/or $R^5$ are other than hydrogen and are a $C_1$–$C_{20}$-, preferably $C_1$–$C_{10}$-alkyl group, a $C_6$–$C_{20}$-, preferably $C_6$–$C_{12}$-aryl group, a $C_2$–$C_{10}$-, preferably $C_2$–$C_4$-alkenyl group, a $C_7$–$C_{40}$-, preferably $C_7$–$C_{10}$-arylalkyl group, a $C_7$–$C_{40}$-, preferably $C_7$–$C_{12}$-alkylaryl group or a $C_8$–$C_{40}$-, preferably $C_8$–$C_{12}$-arylalkenyl group, it also being possible for these radicals to be halogenated.

$R^3$, $R^4$ or $R^5$ are particularly preferably methyl, trifluoromethyl, ethyl, propyl, butyl, pentyl, hexyl, heptyl, octyl, nonyl, decyl, benzyl, phenyl, tolyl, mesityl or xylyl.

$R^4$ or $R^5$ may alternatively be hydrogen; if this is the case, $R^5$ is preferably hydrogen.

$R^6$ is

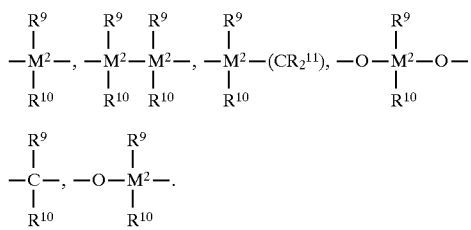

$=BR^9$, $=AlR^9$, —Ge—, —Sn—, —O—, —S—, =SO, $=SO_2$, $=NR^9$, =CO, $=PR^9$ or $=P(O)R^9$, where $R^9$, $R^{10}$ and $R^{11}$ are identical or different and are a hydrogen atom, a halogen atom, a $C_1$–$C_{10}$-, preferably $C_1$–$C_4$-alkyl group, in particular a methyl group, a $C_1$–$C_{10}$-fluoroalkyl group, preferably a $CF_3$ group, a $C_6$–$C_{10}$-, preferably $C_6$–$C_8$-aryl group, a $C_6$–$C_{10}$-fluoroaryl group, preferably a pentafluorophenyl group, a $C_1$–$C_{10}$-, preferably $C_1$–$C_4$-alkoxy group, in particular a methoxy group, a $C_2$–$C_{10}$-, preferably $C_2$–$C_4$-alkenyl group, a $C_7$–$C_{40}$-, preferably $C_7$–$C_{10}$-arylalkyl group, a $C_8$–$C_{40}$-, preferably $C_8$–$C_{12}$-arylalkenyl group or a $C_7$–$C_{40}$-, preferably $C_7$–$C_{12}$-alkylaryl group, or $R^9$ and $R^{10}$ or $R^9$ and $R^{11}$, in each case together with the atoms connecting them, form a ring.

$M^2$ is silicon, germanium or tin, preferably silicon or germanium.

$R^6$ is preferably $=CR^9R^{10}$, $=SiR^9R^{10}$, $=GeR^9R^{10}$, —O—, —S—, =SO, $=PR^9$ or $=P(O)R^9$ and particularly preferably $=SiR^9R^{10}$.

$R^7$ and $R^8$ are identical or different and are as defined for $R^9$.

m and n are identical or different and are zero, 1 or 2, preferably zero or 1, where m plus n is zero, 1 or 2, preferably zero or 1.

The particularly preferred metallocenes are thus the compounds of the formula A

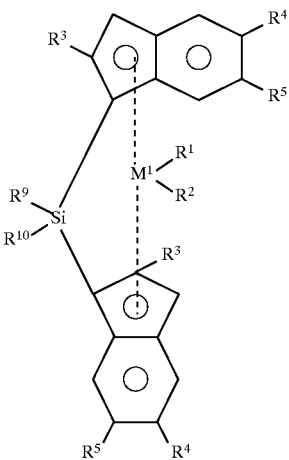

where $M^1$ is Zr or Hf, in particular Zr; $R^1$ and $R^2$ are identical or different and are $(C_1$–$C_3)$-alkyl or chlorine; $R^3$ and $R^4$ are identical or different and are $(C_1$–$C_{10})$-, preferably $(C_1$–$C_4)$-alkyl, which may be halogenated, in particular methyl or butyl, or $(C_6$–$C_{10})$-aryl, in particular phenyl; $R^5$ is hydrogen, $(C_1$–$C_{10})$-, in particular $(C_1$–$C_4)$-alkyl, which may be halogenated, or $(C_6$–$C_{10})$-aryl, in particular phenyl; and $R^9$ and $R^{10}$ are identical or different and are $(C_1$–$C_{10})$-, preferably $(C_1$–$C_4)$-alkyl, in particular methyl, or $(C_6$–$C_{10})$-, preferably $(C_6$–$C_8)$-aryl, in particular phenyl.

The chiral metallocenes are preferably employed as a racemate. However, it is also possible to use the pure R- or S-form. By means of these pure stereoisomeric forms, optically active polymer can be prepared. However, the meso-form of the metallocenes should be separated off, since the polymerization-active center (the metal atom) in these compounds is no longer chiral due to mirror symmetry at the central metal and is therefore incapable of producing a highly isotactic polymer. If the meso-form is not separated off, atactic polymer is formed in addition to isotactic polymers. For certain applications—for example soft moldings—this may be entirely desirable.

Resolution of the stereoisomers is known in principle.

The above-described metallocenes can be prepared in accordance with the following reaction scheme:

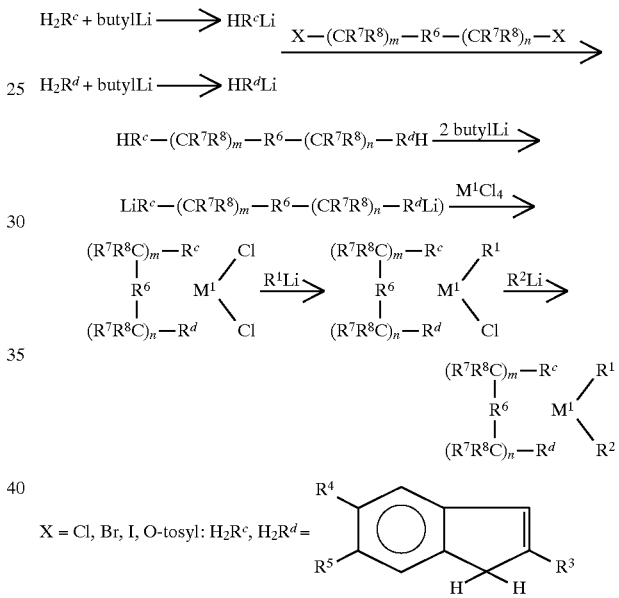

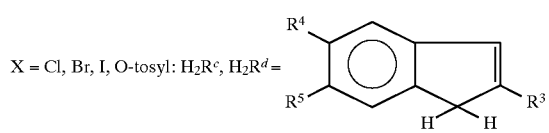

The preparation processes are known from the literature; cf. Journal of Organometallic Chem. 288 (1985) 63–67, EP-A 320 762 and the working examples.

Starting compounds $H_2R^c$ and $H_2R^d$ are prepared, for example, as described in the working examples.

The cocatalyst used according to the invention is preferably an aluminoxane of the formula (II)

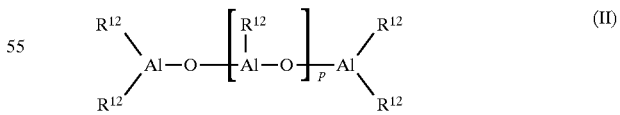

for the linear type and/or of the formula (III)

for the cyclic type, where, in the formulae (II) and (III), the radicals $R^{12}$ may be identical or different and are a $C_1$–$C_6$-alkyl group, a $C_6$–$C_{18}$-aryl group, benzyl or hydrogen, and p is an integer from 2 to 50, preferably from 10 to 35.

The radicals $R^{12}$ are preferably identical and are methyl, isobutyl, phenyl or benzyl, particularly preferably methyl.

If the radicals $R^{12}$ are different, they are preferably methyl and hydrogen or alternatively methyl and isobutyl, where hydrogen and isobutyl are preferably present to the extent of 0.01–40% (number of radicals $R^{14}$).

The aluminoxane can be prepared in various ways by known processes. One of the methods is, for example, to react an aluminum hydrocarbon compound and/or a hydridoaluminum hydrocarbon compound with water (in gas, solid, liquid or bound form—for example as water of crystallization) in an inert solvent (such as, for example, toluene). In order to prepare an aluminoxane containing different alkyl groups $R^{12}$, two different trialkylaluminum compounds ($AlR_3 + AlR'_3$), in accordance with the desired composition, are reacted with water (cf. S. Pasynkiewicz, Polyhedron 9 (1990) 429 and EP-A 302 424).

The precise structure of the aluminoxanes II and III is unknown.

Depending on the preparation method, all aluminoxane solutions have in common a varying content of unreacted aluminum starting compound, which is in free form or as an adduct.

It is possible to preactivate the metallocene by means of an aluminoxane of the formula (II) and/or (III) before use in the polymerization reaction. This significantly increases the polymerization activity and improves the grain morphology.

The preactivation of the transition-metal compound is carried out in solution. The metallocene is preferably dissolved in a solution of the aluminoxane in an inert hydrocarbon. Suitable inert hydrocarbons are aliphatic or aromatic hydrocarbons. Preference is given to toluene.

The concentration of the aluminoxane in the solution is in the region of about 1% by weight to the saturation limits, preferably from 5 to 30% by weight, in each case based on the total solution. The metallocene can be employed in the same concentration, but is preferably employed in an amount of from $10^{-4}$ to 1 mol per mole of aluminoxane. The preactivation time is from 5 minutes to 60 hours, preferably from 5 to 60 minutes. The reaction temperature is from $-78°$ C. to $100°$ C., preferably from $0°$ to $70°$ C.

The metallocene can also be prepolymerized or applied to a support. For the prepolymerization, the (or one of the) olefin(s) employed in the polymerization is preferably used.

Examples of suitable supports are silica gels, aluminum oxides, solid aluminoxane or other inorganic support materials. Another suitable support material is a polyolefin powder in finely divided form.

Compounds of the formulae $R_xNH_{4-x}BR'_4$, $R_xPH_{4-x}BR'_4$, $R_3CBR'_4$ or $BR'_3$ can be used according to the invention as suitable cocatalysts instead of or in addition to an aluminoxane. In these formulae, x is a number from 1 to 4, preferably 3, and the radicals R are identical or different, preferably identical, and are $C_1$–$C_{10}$-alkyl or $C_6$–$C_{18}$-aryl, or 2 radicals R, together with the atom connecting them, form a ring, and the radicals R' are identical or different, preferably identical, and are $C_6$–$C_{18}$-aryl, which may be substituted by alkyl, haloalkyl or fluorine.

In particular, R is ethyl, propyl, butyl or phenyl and R' is phenyl, pentafluorophenyl, 3,5-bistrifluoromethylphenyl, mesityl, xylyl or tolyl (cf. EP-A 277 003, EP-A 277 004 and EP-A 426 638).

When the abovementioned cocatalysts are used, the actual (active) polymerization catalyst comprises the product of the reaction of the metallocene and one of said compounds. This reaction product is therefore prepared first, preferably outside the polymerization reactor, in a separate step using a suitable solvent.

In principle, suitable cocatalysts are according to the invention any compounds which, due to their Lewis acidity, are able to convert the neutral metallocene into a cation and stabilize the latter ("labile coordination"). In addition, the cocatalyst or the anion formed therefrom must not undergo any further reactions with the metallocene cation formed (cf. EP-A 427 697).

In order to remove catalyst poisons present in the olefin, purification by means of an alkylaluminum compound, for example $AlMe_3$ or $AlEt_3$, is advantageous. This purification can be carried out either in the polymerization system itself, or the olefin is brought into contact with the Al compound before addition to the polymerization system and subsequently removed again.

The polymerization or copolymerization is carried out in a known manner in solution, in suspension or in the gas phase, continuously or batchwise, in one or more steps, at a temperature of from $-60°$ to $200°$ C., preferably from $30°$ to $80°$ C. Olefins of the formula $R^a$—CH=CH—$R^b$ are polymerized or copolymerized. In this formula, $R^a$ and $R^b$ are identical or different and are a hydrogen atom or an alkyl radical having 1 to 14 carbon atoms. In the preparation of homopolymers, one of the two radicals $R^a$ and $R^b$ is preferably other than hydrogen. However, $R^a$ and $R^b$, together with the carbon atoms connecting them, can form a ring. Examples of such olefins are ethylene, propylene, 1-butene, 1-hexene, 4-methyl-1-pentene, 1-octene, norbornene and norbornadiene. In particular, propylene and ethylene are polymerized.

If necessary, hydrogen is added as molecular weight regulator and/or to increase the activity. The total pressure in the polymerization system is from 0.5 to 100 bar. Polymerization is preferably carried out in the industrially particularly relevant pressure range of from 5 to 64 bar.

The metallocene is used in a concentration, based on the transition metal, of from $10^{-3}$ to $10^{-8}$ mol, preferably from $10^{-4}$ to $10^{-7}$ mol, of transition metal per $dm^3$ of solvent or per $dm^3$ of reactor volume. The aluminoxane is used in a concentration of from $10^{-5}$ to $10^{-1}$ mol, preferably from $10^{-4}$ to $10^{-2}$ mol, per $dm^3$ of solvent or per $dm^3$ of reactor volume. The other cocatalysts mentioned are used in approximately equimolar amounts with respect to the metallocene. In principle, however, higher concentrations are also possible.

If the polymerization is carried out as a suspension or solution polymerization, an inert solvent which is customary for the Ziegler low-pressure process is used. For example, the polymerization is carried out in an aliphatic or cycloaliphatic hydrocarbon; examples of these which may be mentioned are propane, butane, pentane, hexane, heptane, isooctane, cyclohexane and methylcyclohexane.

It is furthermore possible to use a benzine or hydrogenated diesel oil fraction. Toluene can also be used. The polymerization is preferably carried out in the liquid monomer.

If inert solvents are used, the monomers are metered in as gases or liquids.

The polymerization can have any desired duration, since the catalyst system to be used according to the invention exhibits only a slight time-dependent drop in polymerization activity.

The process according to the invention is distinguished by the fact that the metallocenes described give polymers having the desired property profile, preferably in the industrially relevant temperature range between $30°$ and $80°$ C. with high polymerization activity. These polymers preferably have a molecular weight $M_w$ of >80,000, in particular >100,000 g/mol, a melting point of <145° C. and a molecular weight dispersity $M_w/M_n$ of $\leq 3.5$, in particular $\leq 2.8$.

The examples below are intended to illustrate the invention in greater detail.

The following abbreviations are used:

VI=viscosity index in cm$^3$/g $M_w$=weight average molecular weight in g/mol determined by gel permeation $M_w/M_n$=molecular weight dispersity ) chromatography m.p.=melting point, determined by DSC (heating/cooling rate 20° C./min)

II=isotactic index (II=mm+½ mr), determined by $^{13}$C-NMR spectroscopy $n_{iso}$=isotactic block length mr+2 mm.

Synthesis of the metallocenes used in the examples:

General remarks:

All solvents were dried by customary processes, unless otherwise stated. All reagents, apart from dimethyldichlorosilane, were employed without pretreatment. Dimethyldichlorosilane was distilled before use over potassium carbonate in a stream of nitrogen. Some of the reactions were followed by gas chromatography under uniform conditions: temperature program: 120°–220° C., 10° C./min, 220°–270° C., 40° C./min, helium, 200 kPa, column: HP-1, 50 m.

In order to support assignment of $^{13}$C-NMR signals, in some cases DEPT135-NMR spectra were recorded. The phase position is shown in parenthesis after the value for the chemical shift. (0) denoted quaternary C, (+) methyl or methine and (-) methylene.

EXAMPLE 1

Synthesis of rac-dimethylsilanediylbis(2-methyl-5-isobutyl-1-indenyl)zirconium dichloride 1.1 (±)-2-Methyl-5-isobutyl-1-indanone (1)

17.3 g (125 mmol) of aluminum trichloride were added with ice cooling to a solution of 6.7 g (50 mmol) of isobutyl benzene in 30 ml of methylene chloride. 11.9 g (52 mmol) of 2-bromoisobutyryl bromide were subsequently added rapidly, and the mixture was refluxed for 15 hours. The reaction mixture was poured into 100 ml of ice water, 25 ml of conc. aqueous HCl were added, and the mixture was extracted 3 times with 50 ml of diethyl ether in each case. The combined organic phases were washed with 50 ml each of saturated aqueous NaHCO$_3$ solution and NaCl solution and dried (MgSO$_4$). After removal of the solvent on a rotary evaporator, the crude product was chromatographed on 100 g of silica gel (hexane/methylene chloride 1:1), giving 8.4 g (83%) of 1 as a colorless oil.

$^1$H-NMR (100 MHz, CDCl$_3$): 7.2–7.7 (m, 3H, arom. H), 3.35 (dd, H—C(3)), 2.70 (m, H—C(3), H—C(2)), 2.58 (d, CH$_2$Bu$^i$), 1.95 (q, CH—Bu$^i$), 1.25 (d, CH$_3$), 0.93 (d, 2 CH$_3$—Bu$^i$).

1.2. 2-Methyl-6-isobutylindene (2)

2.4 g (62 mmol) of sodium borohydride were added to a solution of 8.3 g (41 mmol) of 1 in 50 ml of tetrahydrofuran/methanol (2:1), and the mixture was stirred at room temperature for 16 hours. 50 ml of conc. aqueous HCl were subsequently added, and the mixture was extracted 3 times with 50 ml of diethyl ether in each case. The combined organic phases were dried (MgSO$_4$) and freed from solvent on a rotary evaporator. The residue was taken up in 100 ml of toluene, 0.4 g of p-toluenesulfonic acid was added, and the mixture was refluxed for 2 hours. The reaction mixture was washed twice with 50 ml of saturated aqueous NaHCO$_3$ solution in each case and freed from solvent on a rotary evaporator. The residue was purified by chromatography on 400 g of silica gel (hexane), giving 7.17 g (95%) of 2 as a colorless oil.

$^1$H-NMR (100 MHz, CDCl$_3$): 6.9–7.1 (m, 3 arom. H), 6.4 (m, H—C(3)), 3.2 (s, 2H—C(1)), 2.45 (d, CH$_2$—Bu$^i$), 2.10 (d, CH$_3$), 1.9 (m, CH—Bu$^i$), 0.95 (d, 2 CH$_3$—Bu$^i$).

1.3. Dimethylbis(2-methyl-5-isobutylindenyl)silane (3)

7.8 ml (19 mmol) of a 2.5 molar solution of butyllithium in hexane were added at room temperature under argon to 3.6 g (19 mmol) of 2 in 50 ml of H$_2$O— and O$_2$-free tetrahydrofuran, and the mixture was subsequently stirred at 50° C. for a further 2 hours until the evolution of gas was complete. The lithium compound prepared in this way was added dropwise over the course of 4 hours at room temperature to a solution of 1.25 g (9.5 mmol) of dichlorodimethylsilane in 50 ml of H$_2$O— and O$_2$-free tetrahydrofuran, and the mixture was stirred at room temperature for a further 15 hours. The solvent was removed on a rotary evaporator, the residue was taken up in 50 ml of diethyl ether and 50 ml of H$_2$O, the phases were separated, and the aqueous phase was extracted twice with 50 ml of diethyl ether in each case. The combined organic phases were dried (MgSO$_4$), and the solvent was removed on a rotary evaporator. Chromatography on 100 g of silica gel (hexane/methylene chloride 20:1) gave, in addition to 2.1 g of starting material, 1.24 g (75%, based on the conversion) of 3 as a colorless solid. The $^1$H-NMR showed that a mixture of diastereoisomers was present.

$^1$H-NMR (100 MHz, CDCl$_3$): 6.8–7.6 (m, 6 arom. H), 6.6 (m, H—C(3)), 3.8 (m, H—C(1)), 2.6 (d, 2 CH$_3$), 2.3 (d, CH$_2$Bu$^i$), 0.9 (m, CH$_3$—Bu$^i$), -0.2 (m, Si(CH$_3$)$_2$).

1.4. rac-Dimethylsilanediylbis(2-methyl-5-isobutylindenyl) zirconium dichloride (4)

2.3 ml (6 mmol) of a 2.5 molar solution of butyllithium in hexane were added at room temperature under argon to 1.24 g (3 mmol) of 3 in 50 ml of H$_2$O— and O$_2$-free tetrahydrofuran, and the mixture was subsequently stirred at 50° C. for a further 2 hours until the evolution of gas was complete. The solvent was removed under the vacuum of an oil pump, the residue was suspended in H$_2$O— and O$_2$-free hexane, and the suspension was filtered through a G3 frit. The extremely air-sensitive residue was dried for a number of hours under the vacuum of an oil pump and subsequently added to a suspension, pre-cooled to -78° C., of 0.67 g (3 mmol) of zirconium tetrachloride in 50 ml of H$_2$O— and O$_2$-free methylene chloride. The mixture was warmed to room temperature over the course of 15 hours, stirred at room temperature for a further hour and filtered through a G3 frit, and the solid was washed with 30 ml of H$_2$O— and O$_2$-free hexane. The filtrate was freed from solvent under the vacuum of an oil pump and recrystallized from a little H$_2$O— and O$_2$-free hexane, giving 120 mg (7%) of rac-(4) as yellow crystals.

$^1$H-NMR (100 MHz, CDCl$_3$): 7.0–7.5 (m, 6 arom. H), 6.9 (s, H—C(3)), 2.3 (d, CH$_2$—Bu$^i$), 2.1 (s, 2 CH$_3$), 1.9 (m, CH—Bu$^i$), 1.1 (s, Si(CH$_3$)$_2$), 0.9 (m, CH$_3$—Bu$^i$). Molecular weight: 586$^+$, correct decomposition pattern.

EXAMPLE 2

Synthesis of rac-methylphenylsilanediylbis-(2-methyl-5-isobutyl-1-indenyl)zirconium dichloride 2.1. Methylphenylbis(2-methyl-5-isobutylindenyl)silane (5)

7.6 ml (19 mmol) of a 2.5 molar solution of butyllithium in hexane were added at room temperature under argon to 3.5 g (19 mmol) of 2 in 50 ml of H$_2$O— and O$_2$-free tetrahydrofuran, and the mixture was subsequently stirred at 50° C. for a further 2 hours until the evolution of gas was complete. The lithium compound prepared in this way was added dropwise over the course of 4 hours at room temperature to a solution of 1.81 g (9.5 mmol) of dichloromethylphenylsilane in 50 ml of $H_2O$— and $O_2$-free tetrahydrofuran, and the mixture was stirred at room temperature for a further 15 hours. The solvent was removed on a rotary evaporator, the residue was taken up in 50 ml of diethyl ether and 50 ml of $H_2O$, the phases were separated, and the aqueous phase was extracted twice with 50 ml of diethyl ether in each case. The combined organic phases were dried ($MgSO_4$), and the solvent was removed on a rotary evaporator. Chromatography on 100 g of silica gel (hexane/methylene chloride 9:1) gave, in addition to 1.0 g of starting material, 1.46 g (44%, based on the conversion) of 5 as a colorless solid. The $^1$H-NMR showed that a mixture of diastereoisomers was present.

$^1$H-NMR (100 MHz, $CDCl_3$): 7.0–8.0 (m, 11 arom. H), 6.4, 6.6, 6.8 (3 m, H—(3)), 4.2, 4.0 (2s, H—C(1)), 2.6 (d, 2 $CH_3$), 2.15 (m, $CH_2Bu^i$), 1.9 (m, CH—$Bu^i$), 1.0 (m, $CH_3Bu^i$), −0.1 (m, $SiCH_3$).

2.2. rac-Methylphenylsilanediylbis(2-methyl-5-isobutylindenyl)zirconium dichloride (6)

1.8 ml (4 mmol) of a 2.5 molar solution of butyllithium in hexane were added at room temperature under argon to 1.09 g (2 mmol) of 5 in 50 ml of $H_2O$— and $O_2$-free tetrahydrofuran, and the mixture was subsequently stirred at 50° C. for a further 2 hours until the evolution of gas was complete. The solvent was removed under the vacuum of an oil pump, the residue was suspended in $H_2O$— and $O_2$-free hexane, and the suspension was filtered through a G3 frit. The extremely air-sensitive residue was dried for a number of hours under the vacuum of an oil pump and subsequently added to a suspension, pre-cooled to −78° C., of 0.52 g (2 mmol) of zirconium tetrachloride in 50 ml of $H_2O$— and $O_2$-free methylene chloride. The mixture was warmed to room temperature over the course of 15 hours, stirred at room temperature for a further hour and filtered through a G3 frit, and the solid was washed with 30 ml of $H_2O$— and $O_2$-free hexane. The filtrate was freed from solvent under the vacuum of an oil pump. After the solvent had been stripped off, 0.54 g (41%) of the zirconocene 6 was obtained as a mixture of the racemic and meso forms in a ratio of 1:1. Recrystallization from hexane gives the racemic form.

$^1$H-NMR of the isomer mixture (100 MHz, $CDCl_3$): 6.6–8.2 (m, arom. H, H—C(3)), 2.5 (s, $CH_3$), 2.3 (d, $CH_2Bu^i$), 2.2 (s, $CH_3$), 2.0 (s, $CH_3$), 1.9 (m, CH—$Bu^i$), 1.0–1.5 (m, $SiCH_3$, $CH_3$—$Bu^i$).

Molecular weight: 648$^+$, correct decomposition pattern.

EXAMPLE 3

Synthesis of rac-dimethylsilanediylbis-(2-methyl-5-tert-butyl-1-indenyl)zirconium dichloride 3.1. (±)-2-(4-tert-butylbenzyl)propionic acid (7).

18.8 g (107 mmol) of diethyl methylmalonate were added dropwise at room temperature to a solution of 2.5 g (106 mmol) of sodium in 50 ml of $H_2O$-free EtOH. 25.0 g (110 mmol) of 4-tert-butylbenzyl bromide in 20 ml of $H_2O$-free EtOH were subsequently added dropwise, and the mixture was refluxed for 4 hours. The solvent was stripped off, and 200 ml of $H_2O$ were added to the residue. The organic phase was separated off, and the aqueous phase was saturated with NaCl and extracted twice with 100 ml of diethyl ether in each case. The combined organic phases were dried ($MgSO_4$).

The residue remaining after the solvent had been stripped off was taken up in 50 ml of EtOH and 30 ml of $H_2O$, and 21 g (385 mmol) of KOH were added. The reaction mixture was refluxed for 4 hours. The EtOH was stripped off in vacuo, and the residue was acidified to pH 1 by means of conc. aqueous HCl. The precipitate was filtered off with suction and heated at 250° C. for 30 minutes in a bulb tube with vigorous foaming, giving 18.8 g (83%) of 7 as a viscous oil.

$^1$H-NMR (100 MHz, $CDCl_3$): 11.5 (s, 1H, COOH), 7.0–7.3 (m, 4H, arom. H), 2.7–3.1 (m, 3H, CH and $CH_2$), 1.2 (s, 9H, $Bu^t$), 1.1 (d, 3H, $CH_3$).

3.2. (±)-2-Methyl-6-tert-butylindan-1-one (8)

A solution of 18.7 g (91 mmol) of 7 in 20 ml (280 mmol) of thionyl chloride was refluxed for 3 hours. Excess thionyl chloride was removed at 10 mbar, and the oily residue was freed from adhering residues of thionyl chloride by repeated removal of 100 ml of toluene in each case in vacuo.

The acid chloride was taken up in 50 ml of toluene, and the solution was added dropwise at 10° C. to a suspension of 32 g (241 mmol) of aluminum trichloride in 100 ml of toluene. When the addition was complete, the mixture was refluxed for a further 3 hours. The reaction mixture was poured onto 300 g of ice and acidified to pH 1 by means of conc. aqueous HCl. The organic phase was separated off, and the aqueous phase was extracted 3 times with 100 ml of diethyl ether in each case. The combined organic phases were washed with saturated aqueous $NaHCO_3$ solution and saturated aqueous NaCl solution and dried ($MgSO_4$). The residue remaining after removal of the solvent in vacuo was purified by distillation under the vacuum of an oil pump, giving 5.5 g (33%) of 8 as a colorless oil at 90°–98° C./0.1 mmHg.

$^1$H-NMR (100 MHz, $CDCl_3$): 7.2–7.8 (m, 3H, arom. H), 3.3 (dd, 1H, β-H), 2.5–2.9 (m, 2H, α- and β-H), 1.2 (m, 12H, $Bu^t$ and $CH_3$).

3.3. 2-Methyl-6-tert-butylindene (9)

5.3 g (26 mmol) of 8 were dissolved in 50 ml of tetrahydrofuran/methanol (2:1), 1.5 g of sodium borohydride were added at 0° C. with magnetic stirring, and the mixture was stirred at room temperature for 18 hours. The reaction mixture was poured onto ice, conc. HCl was added to pH 1, and the mixture was extracted a number of times with diethyl ether. The combined organic phases were washed with saturated aqueous $NaHCO_3$ solution and NaCl solution and dried ($MgSO_4$). The solvent was removed in vacuo, and the crude product, without further purification, was taken up in 300 ml of toluene, 0.1 g of p-TsOH was added, and the mixture was refluxed for 1 hour. The reaction mixture was washed with 100 ml of saturated aqueous $NaHCO_3$ solution, and the solvent was removed in vacuo. The crude product was purified by filtration through 200 g of silica gel (hexane), giving 4.8 g (99%) of 9 as a colorless oil.

$^1$H-NMR (100 MHz, $CDCl_3$): 7.0–7.3 (m, 3H, arom. H), 6.4 (m, 1H, H—C(3)), 3.2 (s, 2H, $CH_2$), 2.1 (s, $CH_3$), 1.3 (s, 9H, $Bu^t$).

3.4. Dimethylbis(2-methyl-5-tert-butylindenyl)silane (10)

10.7 ml (26 mmol) of a 2.5 molar solution of butyllithium in hexane were added at room temperature under argon to 4.7 g (26 mmol) of 10 in 30 ml of $H_2O$— and $O_2$-free tetrahydrofuran, and the mixture was subsequently stirred at 50° C. for a further 2 hours until the evolution of gas was complete. The lithium compound prepared in this way was added dropwise over the course of 4 hours at room temperature to a solution of 1.73 g (13 mmol) of dichlorodimethylsilane in 50 ml of $H_2O$— and $O_2$-free tetrahydrofuran, and the mixture was stirred at room temperature for 15 hours. The solvent was removed on a rotary evaporator, the residue was taken up in 50 ml of diethyl ether and 50 ml of H$_2$O, the phases were separated, and the aqueous phase was extracted twice with 50 ml of diethyl ether in each case. The combined organic phases were dried (MgSO$_4$), and the solvent was removed on a rotary evaporator. Flash chromatography on 350 g of flash silica gel (hexane/methylene chloride 9:1) gave 2.0 g (38%) of 10 as a colorless oil. The $^1$H-NMR showed that a mixture of diastereoisomers was present.

$^1$H-NMR (300 MHz, CDCl$_3$): 7.2–7.7 (m, 6H, arom. H), 6.8 (m, 2H, H—C(3)), 3.85 (m, 2H, H—C(1)), 2.40 (m, 6H, CH$_3$), –0.3 (m, 6H, Si(CH$_3$)$_2$).

3.5. rac-Dimethylsilanediylbis(2-methyl-5-tert-butyl-1-indenyl)zirconium dichloride (11)

4 ml (10 mmol) of a 2.5 molar solution of butyllithium in hexane were added at room temperature under argon to 2.0 g (5 mmol) of 3 in 50 ml of H$_2$O— and O$_2$-free tetrahydrofuran, and the mixture was subsequently stirred at 50° C. for a further 2 hours until the evolution of gas was complete. The solvent was removed under the vacuum of an oil pump, the residue was suspended in H$_2$O— and O$_2$-free hexane, and the suspension was filtered through a G3 frit. The extremely air-sensitive residue was dried for a number of hours under the vacuum of an oil pump and subsequently added to a suspension, pre-cooled to –78° C., of 1.2 g (5.1 mmol) of zirconium tetrachloride in 50 ml of H$_2$O— and O$_2$-free methylene chloride. The mixture was warmed to room temperature over the course of 15 hours, stirred at room temperature for a further hour and filtered through a G3 frit, and the solid was washed with 30 ml of H$_2$O— and O$_2$-free hexane. The filtrate was freed from solvent under the vacuum of an oil pump, and the residue was recrystallized from a little H$_2$O— and O$_2$-free hexane, giving 1.05 g (37%) of the zirconocene 11 as a mixture of the racemic and meso forms in the ratio 1:1. Repeated recrystallization from hexane gives the racemic form.

$^1$H-NMR (100 MHz, CDCl$_3$): 7.0–7.6 (m, 6 arom. H), 6.8 (s, H—C(3)), 2.1 (s, 2 CH$_3$), 1.0–1.3 (m, Si(CH$_3$)$_2$ and CH$_3$—Bu$^t$). Molecular weight 588$^+$, correct decomposition pattern.

EXAMPLE 4

Synthesis of rac-dimethylsilanediylbis-(2,5,6-trimethyl-1-indenyl)zirconium dichloride 4.1. 3,4-Dimethylpropiophenone (12)

534 g (4 mol) of dry aluminum chloride are stirred with 500 ml of absolute o-xylene. The apparatus is placed in an ice bath, and the dropwise addition of 260 g (2 mol) of propionic anhydride is begun at an internal temperature of 5° C. During this addition, the temperature must not exceed 10° C. When the dropwise addition is complete (about 5 hours), the mixture is left to stir overnight. The solution, which is now dark red, is worked up by pouring onto 1 kg of ice. A milky yellow organic phase separated out. The mixture is stirred for a further hour. During this time, the organic phase becomes clear, and it is separated off in a separating funnel, washed with water and then dried over sodium sulfate. First, excess xylene is removed by distillation in vacuo (10 mmHg), then a short Vigreux column is attached and the 3,4-dimethylpropiophenone is removed by distillation in vacuo (4.5 mmHg). Yield 225 g, 69% (based on propiophenone), b.p. 94° C. (4.5 mmHg).

Gas chromatography: 11.02 min; $^1$H-NMR (CDCl$_3$, 100 MHz, RT): 7.5 s(2H), 7.06, s(1H), 6.98 s(1H), 2.78 m(2H), 2.13 s(6H), 1.06 t(3H); $^{13}$C-NMR (CDCl$_3$, 100 MHz, RT): 199.76(0), 141.83(0), 136.4(0), 134.5(0), 129.37(+), 128.91 (+), 125.36(+), 31.23(–), 19.53(+), 19.40(+), 7.99(+); Mass spectrum: M$^+$: 162, B: 133, 147, 115, 105, 91, 77, 63, 51, 28; IR spectrum (film, KBr disks): 3030w, 2978s, 2936s, 2883s, 1682vs, 1608s, 1571m, 1526s, 1454m, 1411m, 1383w, 1350s, 1242s, 1213m, 1176m, 1143m, 1022m, 963m, 904vw, 888vw, 863w, 850w, 797vs, 741vw, 706s, 681w.

4.2. 1-(3,4-Dimethylphenyl)-1-oxo-2-methyl-3-dimethylaminopropane (13)

A. Mannich salt: 162 g (1 mol) of 3,4-dimethylpropiophenone (12) is refluxed for 6 hours with 30 g of paraformaldehyde, 97.86 g (1.2 mol) of dimethylamine hydrochloride in 500 ml of ethanol. Half of the ethanol is then removed by distillation on a rotary evaporator, and the remainder of the solution is left to crystallize at –30° C. The crystal slurry produced is filtered off with suction and washed with acetone. The mother liquor is evaporated again and again left to crystallize. The combined crystalline material is recrystallized from ethanol. 255 g (78%).

$^1$H-NMR (400 MHz, CDCl$_3$, RT) 7.6 s(1H), 7.58, 7.56 d, J=7.93 Hz(1H), 7.14, 7.12 d, J=7.93 Hz(1H), 3.96 m(1H), 3.53, 3.5, 3.49, 3.47 dd, J$_{gem}$=12.18 Hz, J=10.14 Hz(1H), 3.08, 3.07, 3.05, 3.04 dd, J$_{gem}$=12.82 Hz, J=5.01 Hz(1H), 2.7 s(br)(1H), 2.53 s(6H), 2.10 "s"(6H), 1.075, 1.057 d, J=7.32 Hz(3H); IR spectrum (KBr disk): 3469w, 3019w, 2971w, 2918m(br), 2865sh, 2781sh, 2628m-(br), 2475m, 1672vs, 1604m, 1576m, 1560m, 1482s, 1456m, 1419s, 1382m, 1329s, 1240s, 1192m, 1171m, 1113m, 991s, 933w, 902w, 891w, 860w, 836s, 765w, 627w, B. Isolation of the free base: 134 g (0.52 mol) of the Mannich salt (4.2.A) are stirred in 3–5 g portions into an ice-cooled solution of 60 g of KOH (1.04 mol) in 200 ml of distilled water. A little ether is occasionally added in order to prevent clumping and the consequent reduction in the reaction rate. The mixture is left to stir for about 12 hours, and the organic phase is then separated off. The ether is evaporated, and the resultant oil is immediately processed further. Yield 109 g (96%).

In an alternative method, the corresponding amount of sodium hydroxide is finely powdered in a mortar. The Mannich salt in small portions is then stirred in with rapid grinding. The composition becomes warm and pasty. The more Mannich salt is added, the more liquid the composition becomes. The ultimately runny oil is transferred into a conical flask and stirred for a further 2 hours. Yield 109 g (96%).

4.3. 3,4-Dimethylphenyl 2-methylvinyl ketone (14)

121 g (0.55 mol) of the free Mannich base (13) are brought into intimate contact with 45 g (0.33 mol) of anhydrous zinc chloride by vigorous stirring, which should be carried out in vacuo. The mixture is then distilled at 4.5 mmHg, during which the contents of the distillation flask become increasingly intense yellow. The distillation is continued until the temperature of the distillate passing over increases to above 120° C. Yield 76 g (78%), 112° C. (4.5 mmHg).

Gas chromatography 11.39 min; $^1$H-NMR (100 MHz, CDCl$_3$, RT): 7.26 s(1H), 6.9 s(1H), 5.57 s(1H), 5.31 s(1H), 2.02 d(shoulder)(6H), 1.78 s(3H); $^{13}$C-NMR (CDCl$_3$, 100 MHz, RT): 197.76, 143.46, 141.11, 136.15, 134.92, 130.18, 128.95, 126.9, 125.60, 19.53, 19.28, 18.38, Mass spectrum (70 eV, EI): 174 M, 133 B, 159, 146, 118, 105, 77, 63, 52, 39, 27. IR spectroscopy (film in KBr plates): 3095w, 3024w, 2975m, 2948m, 2923m, 2877sh, 1654vs, 1625m, 1608s, 1571w, 1497w, 1451s, 1408m, 1338w, 1371w, 1328s, 1236m, 1205m, 1163m, 1122s, 1033m, 884m, 935m(br), 901w, 870w, 849w, 830w, 793s.

Alternative method: 53 g (0.25 mol) of freshly prepared amine are dissolved in 300 ml of acetone. 34 g (15 ml, 0.28 mol) of methyl iodide are added dropwise at 5° C. (cooling in an ice bath) over the course of one hour. White flakes are precipitated soon after the addition is commenced. When the addition is complete, the mixture is left to stir for about 10 hours, during which time a thick white material deposits. The powder is separated off with the aid of a suction filter, and the mother liquor is concentrated to half the volume and then placed in a refrigerator. The crystalline material which deposits is combined with the main portion and washed with cold acetone. Yield 80 g (93%). The trimethylammonium salt obtained in this way is dissolved in 600 ml of water to which 40 g of sodium hydrogencarbonate have been added. A layer of 200 ml of ether is added, and the mixture is stirred overnight. The organic phase is then separated off in a separating funnel and distilled. Yield 37 g, 94%.

4.4. 2,5,6-Trimethyl-1-oxoindane and 2,6,7-trimethyl-1-oxoindane (15)

150 ml of conc. sulfuric acid are cooled to 0° C. 50 g (0.28 mol) of 3,4-dimethylphenyl 2-methylvinyl ketone (14) are then added dropwise over the course of half an hour. The liquid becomes an intense red color within minutes. When the addition is complete, the flask is removed from the ice bath and left to stir for a further 20 minutes. During this time, warming to 40°–50° C. is observed. The mixture is worked up by pouring onto ice, and the emulsion is extracted three times with 100 ml of ether. The combined organic phases are dried by means of magnesium sulfate and evaporated.

Alternative methods (isomer determination by gas chromatography):

1) 50 g of phosphorus pentoxide are added to 176 g of syrupy phosphoric acid. During the addition, the mixture is cooled in an ice bath and the time intervals between the additions are selected so that the temperature does not exceed 60° C. At 40° C., 36 g (0.2 mol) of the vinyl ketone are added in one portion. The temperature rises to 55° C., and then remains constant for up to 2 hours. When the warming has subsided, the dark-orange material is worked up as described above.

2) 150 ml of methanesulfonic acid are cooled to 0° C. 36 g (0.2 mol) of the vinyl ketone are slowly added dropwise to the cold solution. When the addition is complete, the flask is removed from the ice bath. The temperature rises to room temperature in a short time (about 5 minutes) and is kept at this temperature by further cooling in the ice bath. Work-up as above.

Gas chromatography 12.6 min (2,5,6-trimethyl-1-oxoindane)/12.84 min (2,4,5-trimethyl-1-oxoindane);

Mass spectrum (GC-MS) 174 M, 159 B, 146, 131, 115, 103, 91, 77, 63, 52, 39, 27. The two isomers differ in the mass spectrum only in the ratio between the intensities of the peak of mass 146 and the intensity of the base peak and with the peak of mass 131.

4.5. 2,5,6-Trimethyl-1-hydroxyindane (16)

Variant A: 48 g (0.27 mol) of the indanone mixture (15) obtained in section 4.4. are dissolved in 400 ml of methanol, and the solution is cooled to 0° C. A total of 10.75 g (0.27 mol) of sodium borohydride are added in 1 g portions at intervals of 10 minutes. Towards the end of the addition, the time intervals are increased. The mixture is stirred until the evolution of gas has subsided, and conc. hydrochloric acid is then added dropwise until evolution of gas is no longer observed. Dilution with 750 ml of water gives a flocculent precipitate, which is filtered off with suction. The filtrate is extracted with ether. The white precipitate comprises the mixture of isomeric indanols. Pure 2,5,6-trimethylindanol is isolated as follows: 7.5 g of the precipitate are dissolved in boiling hexane to saturation (53 ml). The solution is allowed to cool by standing untouched, during which short needle-shaped crystals deposit. The crystallization process is terminated by pouring off the mother liquor when the solution is still luke-warm. The crystal material contains only about 18% of the 2,6,7-trimethylindanol isomer. It is again recrystallized from hexane, but with 20% more solvent than necessary for the saturation concentration and is left to stand for a few hours, during which long crystal needles deposit. This product contains only 2% of the undesired isomer.

Variant B: 48 g (0.27 mol) of the indanone mixture (15) are dissolved in 250 ml of methanol, and the solution is cooled to 0° C. A total of 10.75 g (0.27 mol) of sodium borohydride are added in 1 g portions at intervals of 10 minutes. Towards the end of the addition, the time intervals are increased. When about 4–5 g of sodium borohydride have been added, the solution becomes unclear. When the addition is complete, the mixture is stirred for about 12 hours, and the fine powder formed is then filtered off with suction. The filtrate is treated as described under variant A. Yield 10 g, 23% (pure 2,5,6-trimethylindanol).

$^1$H-NMR (100 MHz, $CDCl_3$, RT): 7.13 s(1H), 6.97 s(1H), 4.64 s(1H, broad), 3.0 m(1H), 2.4 m(1H), 2.22 s(6H), 1.13 d, J=6.44 Hz, (3H). $^{13}$C-NMR ($CDCl_3$, 100 MHz, RT): 142.6(0), 139.6(o), 136.5(0), 134.9(0), 125.9(0), 124.9(+), 82.8(+), 45.5(+), 37.5(−), 19.84(+), 19.77(+), 17.93(+); IR spectrum (KBr disk) 3352vs(br), 3010m, 2961m, 2932m, 2907m, 2845m, 1491m, 1450s, 1376w, 1353m, 1330m, 1307, 1282w, 1257w, 1232w, 1195w, 1166w, 1125w, 1080ss, 1031s, 993m, 973w, 940w, 903w, 891m, 874s, 833m, 759w, 640w, 603w(br), 442m.

4.6. 2,5,6-Trimethylindene (17)

2.67 g of 2,5,6-trimethyl-1-hydroxyindane (16) from section 4.5. are suspended in a solution of 15 g of oxalic acid in 100 ml of distilled water. The suspension is then refluxed for 30 minutes. When a white deposit can be seen to have formed on the wall of the condenser, the boiling is terminated and a distillation bridge with a broad condenser tube is attached. Water is squeezed out of the crystalline material, which is then dried over $CaCl_2$, giving a white, strongly smelling substance. Yield 2 g, 83%, analysis: calc. for $C_{12}H_{14}$, (158.2): C 91.13, H 8.8; found: C 90.63, H 9.0.

Gas chromatography: RT: 10.8 min; $^1$H-NMR (100 MHz, $CDCl_3$, RT): 7.31 s(1H), 7.21 s(1H), 6.59 s(1H), 3.38 s(2H), 2.46 s(6H), 2.3 s(3H); $^{13}$C-NMR ($CDCl_3$, 100 MHz, RT) 144.77(0), 143.85(0), 141.0(0), 133.95(0), 131.36(0), 126.8 (+), 124.64(+), 120.88(+), 42.2(−), 19.8(+), 19.72(+), 16.61 (+); Mass spectrum (70 eV, EI) 158 M, 143 B, 128, 115, 102, 89, 77, 63, 52, 39, 28; IR spectrum (KBr disk) 3060w, 3013w, 2961w, 2909m, 2852m, 1621w, 1604w, 1473s, 1450s, 1384s, 1345sh, 1289w, 1254w, 1206m, 1175w, 1128w, 1020m, 996m(br), 919w, 880s(br), 818w, 756w, 721m, 613m, 555w, 427ss.

4.7. 2,5,6-Trimethylindenyldimethylchlorosilane (18)

2.33 g (14 mmol) of the very well dried indene (17) are dissolved in 50 ml of hexane. After the solution has been cooled to 0° C. in an ice bath, 7 ml of 2M n-butyllithium are added (14 mmol). The mixture is stirred for 3 hours, during which a thick, pale yellow precipitate forms. The lithium salt is filtered off with suction and washed three times with hexane. 6 ml of dimethyldichlorosilane (freshly distilled over potassium carbonate) in 50 ml of ether are cooled to −35° C. The dry lithium salt is introduced in portions into this solution. Initially everything dissolves; the solution later becomes cloudy. The mixture is warmed to room temperature and stirred for about a further 12 hours. The ether is stripped off in vacuo to ¼ of the volume, and the precipitate lithium chloride is filtered off with suction. The pale lemonyellow liquid is evaporated to an oily consistency and then left to stir in vacuo for a few hours.

$^1$H-NMR (400 MHz, CDCl$_3$, RT) 7.35 s(1H), 7.2 s(1H), 6.63 s(1H), 3.55 s(1H), 2.4 m(9H), 0.52 s(3H), 0.23 s(3H) s(3H); $^{13}$C-NMR (CDCl$_3$, 400 MHz, RT) 144.47(0), 143.36 (0), 140.12(0), 133.83(0), 131.11(0), 127.05(+), 124.6(+), 121.05(+), 49.26(+), 20.08(+), 19.93(+), 17.47(+), 1.04(+), −0.77(+); Mass spectrometry (70 eV, EI) 65.1(6.1%), 77.1 (2.3), 93.1(B), 94.1(6.9), 95.0(34.7), 115.1(9.2), 128.0(9.2), 141.3(24.5), 142.2(15.6), 143.2(15.0), 155.2(8.9), 156.2 (72.8), 157.3(32.3), 158.3(19.6), 235.0(1.8), 250.4(61.2)M, 251.3(12.5)M, 252.3(22.3)M, 253.4(4.2)M 4.8. Bis(2,5,6-trimethylindenyl)dimethylsilane (19)

2.61 g (10 mmol) of the indenyldimethylchlorosilane (18) prepared in section 4.7. are dissolved in 60 ml of ether. 1.77 g of the indenyllithium salt (section h) are added to this solution. 30 ml of THF are also added at 0° C., and the mixture is then allowed to warm and is stirred for about 12 hours. The flocculent indenyllithium dissolves on addition of THF, and at the same time a pale reddish pastel shade appears. Soon thereafter, microcrystalline lithium chloride precipitates. In order to monitor the reaction by NMR spectroscopy, two or three samples are taken. The appearance or disappearance of the 3 or 2 peaks at −0.39 or 0.62/0.34 ppm (chlorosilane) allows the progress of the reaction to be monitored. The solvent is stripped off to 30 ml, and the liquid is separated from the lithium chloride. 20–30 g of silica gel G-60 are then added to the liquid. The solid is freed from the solvent. A 10 cm layer of silica gel G-60 is poured into pentane in a G-3 frit (3 cm). The previously prepared silica gel/product mixture is then added. 100 ml of pentane are added, and the eluate is discarded. A yellowish zone is then eluted with pentane:methylene chloride (100 ml+5 ml). The methylene chloride concentration is increased to 10/1, and then to 10/2, and in each case 100 ml thereof are employed.

The final 30 to 40 ml of eluate before the yellow zone are collected separately; they contain unreacted indene. The yellow eluate deposits fine white crystals on evaporation. These are filtered off with suction and dried and are pure diastereomer. The mother liquor is subjected to further chromatographic purification. Yield 1.2 g (32%). By reducing the amount of solvent to ⅓, pure diastereomer can be isolated from the large amount of precipitate produced after filtration through the frit and drying by extraction with methylene chloride. Chromatographic purification is then unnecessary. Yield 1.6 g (45%). The mother liquor is worked up as described above. Total yield 2.5 g (67%). Analysis: calc. for C$_{26}$H$_{32}$Si: C 83.8, H 8.6, Si 7.5; found: C 83.2, H 8.9, Si 7.3.

$^1$H-NMR (100 MHz, CDCl$_3$, RT) 7.18 s(2H), 7.07 s(2H), 6.48 s(2H), 3.57 s(2H), 2.23 s(6H), 2.19 s(6H), 2.11 s(6H), −0.39 s(6H) a diastereomer; $^{13}$C-NMR (CDCl$_3$, 100 MHz, RT) 145.97(0), 143.43(0), 142.62(0), 133.2(0), 130.2(0), 130.85(0), 126.36(+), 124.47(+), 120.97(+), 46.51(+), 20.12 (+), 19.94(+), 17.86(+), 0.94(+); Mass spectrometry (70 eV, EI) 59.3(49.1), 84.1(2.2), 115.1(1.1), 128.1(1.3), 141.2(5.6), 142.3(5.4), 143.2(2.1), 145.3(1.0), 155.3(10.7), 156.2(4.5), 157.2(5.4), 171.1(1.3), 172.1(0.7), 173.1(9.7), 174.1(2.3), 175.1(1.0), 185.1(4.1), 186.2(6.0), 186.7(1.7), 187.1(25.8), 188.1(4.7), 197.3(1.3), 199.1(4.4), 200.3(4.4), 214.3(3.9), 215.3(100.0; B), 216.3(47.6), 217.3(12.0), 218.3(1.3), 372.3 (45.0)M, 373.4(14.6)M, 374.4(3.7)M; IR spectrum (KBr disk) 3058w, 3004m, 2960m, 2921s, 2858m, 1588m, 1468s, 1438m, 1411sh, 1379w, 1293w, 1248s, 1181w, 1164m, 1120m, 1099sh, 1038vs, 1008vs, 913m, 875vs, 844m, 816vs, 778m, 742w, 702w, 669vw, 637w, 622vw 4.9 rac-Dimethylsilanediylbis(2,5,6-trimethyl-1-indenyl) zirconium dichloride (20)

0.80 g (2.16 mmmol) of the bis(2,5,6-trimethyl-1-indenyl)dimethylsilane (19) are dissolved in 100 ml of an ether/THF mixture (2+1 parts by volume). 2.68 ml of n-butyllithium (5.37 mmol, 25% excess) are added dropwise, during which the solution becomes a red color. After 4–5 hours, the solution is evaporated to dryness in vacuo. The foamy material is broken up coarsely using a spatula and stirred with 10 ml of ether, during which the color suddenly changes to beige. Stripping-off of the solvent gives a fine powder, which is slurried three times with hexane. As long as the liquid is a yellow color, it is stripped off via a frit. When the filtrate is colorless, the dilithio salt is dried in vacuo. 550 mg of ZrCl$_4$ are added to 50 ml of methylene chloride. The suspension is cooled to −50° C. The dilithio salt is then added in portions. The suspension soon becomes an orange color. It is allowed to warm over a period of 3–4 hours and is stirred overnight. An intense orange solution with a fine precipitate has formed. The solution is filtered, and the filtrate is evaporated in vacuo. 15 ml of toluene and 4–5 ml of hexane are added to the yellow dust. Again a precipitate forms which is no longer soluble in organic media. It is again filtered, dried and again dissolved in methylene chloride/hexane, 3 ml of hexane being initially introduced and increasing amounts of methylene chloride being added until the maximum solubility has been reached. A further filtration gives a solution from which a yellow microcrystalline powder is formed on evaporation. This powder is decanted off and dried in vacuo.

Alternative work-up method:

The reaction solution is transferred onto a frit, the liquid is stripped off, and the frit contents are extracted 4× with a hexane/methylene chloride (1+1, 40 ml) solvent mixture. These extracts are combined, and the solvent is stripped off until cloudiness forms. The solution is placed in the refrigerator overnight at −30° C.

The orange crystal deposit which has formed on the walls of the Schlenk tube after about 2 hours is dissolved in just the sufficient amount of methylene chloride, a further 2 ml are added, and the product is left to crystallize again for a few days by cooling to −36° C. This very pure meso product is treated with a few ml of toluene and is warmed to about 60° C. When everything has dissolved, the Schlenk tube is placed in a Dewar vessel containing warm water at the same temperature. After about a week, rhombic crystals of the meso product are obtained.

Analysis: calc. for C$_{26}$H$_{30}$SiCl$_2$Zr. ½CH$_2$Cl$_2$ (483.44): C 55.0, H 5.34, Zr 16.0; found: C 55.35, H 5.34, Zr 15.93. $^1$H-NMR (400 MHz, CDCl$_3$, RT) 7.38 s(2H), 7.19 s(2H), 6.53 s(2H), 2.38 s(6H), 2.22 s(6H), 2.13 s(6H), 1.4 s(3H), 1.16 s(3H); $^{13}$C-NMR (CDCl$_3$, 400 MHz, RT) 136.83, 136.23, 135.0, 133.76, 127.3, 125.5, 123.6, 118.55, 83.18, 20.79, 20.32, 18.94, 2.79, 2.69; Mass spectrometry (70 eV, EI) 536(8.9), 535(6.0), 534(19.1), 533(12.7), 532(28.7), 531(14.5), 530(24.6), 216(21.8), 215(100), 519(3.2), 518 (1.8), 517(4.4), 516(2.3), 515(4.3), 373(7.1), 372(18.4), 371 (3.3), 315(4.3), 314(16.5), 252(13.3), 251(10.0), 250(32.4), 249(6.1), 187(13.3), 183(6.8), 173(12.7), 169(8.3), 159 (28.3), 158(91.7), 157(74.2), 156(54.2), 155(19.3), 144 (10.5), 143(73.3), 142(33.2), 141(42.6), 129(11.8), 128 (34.0), 127(8.3), 115(23.8), 95(22.1), 93(65.0), 73(11.4), 71(11.4), 60(47.0), 58(40.1), 57(24.00), 56(19.3), 55(11.8), Alternative method for isolating the two isomers: the amounts of ZrCl$_4$ and dilithio salt indicated at the outset are combined successively in toluene at 0° C., ZrCl$_4$ being introduced first and being stirred at room temperature for 12 hours. The suspension becomes a yellow color after the first additions. The coloration developes into a very intense shade, so that the solution appears dark, as soon as about half of the dilithio salt has been added. The mixture is allowed to settle thoroughly, and the solution is filtered. The orange solution is evaporated to ⅓ of the volume in vacuo and is left to crystallize at −36° C. A yellow fine dust and large orange crystals form. The yellow fine rac compound is separated by shaking and decantation.

Polymerization examples

EXAMPLE 5

A dry 16 dm$^3$ reactor was flushed with nitrogen and charged with 10 dm$^3$ of liquid propylene. 30 cm$^3$ of the toluene solution of methylaluminoxane (corresponding to 40 mmol of Al, mean degree of oligomerization n=19) were then added, and the batch was stirred at 30° C. for 15 minutes. In parallel, 1.8 mg of rac-dimethylsilanediyl-bis(2,5,6-trimethyl-1-indenyl)zirconium dichloride were dissolved in 15 cm$^3$ of a toluene solution of methylaluminoxane (20 mmol of Al), and left to stand for 15 minutes for preactivation. The solution was then introduced into the reactor and heated to 70° C. by supply of heat (10° C./min), and the polymerization system was kept at 70° C. for 1 hour. The reaction was terminated by rapidly removing the excess monomer in gas form. The activity of the metallocene was 27.8 kg of PP/g of metallocene×h.

VI=101 cm$^3$/g; M$_w$=100,000 g/mol; M$_w$/M$_n$=2.5; melting point=130° C.; II=89.0%; n$_{iso}$=16.

EXAMPLE 6

Example 5 was repeated using 4.4 mg of the metallocene, the polymerization temperature was 50° C. and the metallocene activity was 5.2 kg of PP/g of metallocene×h.

VI=181 cm$^3$/g; M$_w$=204,000 g/mol; M$_w$/M$_n$=2.5; melting point=139° C.; II=90.6%; n$_{iso}$=20.

EXAMPLE 7

Example 5 was repeated using 10.0 mg of the metallocene rac-dimethylsilanediylbis(2-methyl-5-isobutyl-1-indenyl) zirconium dichloride. The metallocene activity was 40.0 kg of PP/g of metallocene×h.

VI=144 cm$^3$/g; M$_w$=168,000 g/mol; M$_w$/M$_n$=2.1; melting point=140° C.; II=92.8%; n$_{iso}$=25.

EXAMPLE 8

Example 5 was repeated using 10.0 mg of the metallocene rac-methylphenylsilanediylbis(2-methyl-5-isobutyl-1-indenyl)zirconium dichloride. The metallocene activity was 54.5 kg of PP/g of metallocene×h.

VI=225 cm$^3$/g; M$_w$=289,000 g/mol; M$_w$/M$_n$=2.3; melting point=138° C.; II=91.5%; n$_{iso}$=22.

EXAMPLE 9

Example 5 was repeated using 20.2 mg of the metallocene rac-dimethylsilanediylbis(2-methyl-5-tert-butyl-1-indenyl) zirconium dichloride. The metallocene activity was 59.4 kg of PP/g of metallocene×h.

VI=132 cm$^3$/g; M$_w$=146,000 g/mol; M$_w$/M$_n$=2.2; melting point=139° C.; II=91.0%; n$_{iso}$=22.

EXAMPLE 10

The procedure was as in Example 5, but the propylene was first purified for one hour at room temperature in a stirred 200 dm$^3$ (s.t.p.) reserve lock with 0.5 mmol of AlMe$_3$/dm$^3$ (s.t.p.) of liquid propylene (removal of catalyst poisons) and then condensed into the reactor. The activity of the metallocene was 254 kg of PP/g of metallocene×h.

VI=155 cm$^3$/g; M$_w$=143,000 g/mol; M$_w$/M$_n$=2.2; melting point=132° C.

EXAMPLE 11

The procedure was as in Example 10, but the polymerization temperature was 50° C. The activity of the metallocene was 94.5 kg of PP/g of metallocene×h.

VI=268 cm$^3$/g; M$_w$=332,500 g/mol; M$_w$/M$_n$=2.4; melting point=139° C.

EXAMPLE 12

The procedure was as in Example 10, but the polymerization temperature was 30° C. The activity of the metallocene was 41 kg of PP/g of metallocene×h.

VI=396 cm$^3$/g; M$_w$=419,500 g/mol; M$_w$/M$_n$=2.1; melting point=144° C.

EXAMPLE 13

The procedure was as in Example 10, but in addition 2.5 dm$^3$ (s.t.p.) of hydrogen were metered into the reactor before the polymerization (molecular weight regulation). The activity of the metallocene was 302.5 kg of PP/g of metallocene×h.

VI=104 cm$^3$/g; M$_w$=102,500 g/mol; M$_w$/M$_n$=2.0; melting point=134° C.

EXAMPLE 14

The procedure was as in Example 10, but in addition 15 kg of ethylene were metered in continuously during the polymerization. The metallocene activity was 235 kg of ethylene-propylene copolymer/g of metallocene×h.

VI=98 cm$^3$/g; melting point=123° C.; ethylene content (by IR analysis)=2.8% by weight.

EXAMPLE 15

A dry 150 dm$^3$ reactor was flushed with propylene and charged at 20° C. with 80 dm$^3$ of a benzine fraction having the boiling range 100°–120° C. from which the aromatic components had been removed. 50 l of liquid propylene were added, followed by 64 cm$^3$ of a toluene solution of methylaluminoxane (corresponding to 100 mmol of Al, mean molecular weight according to cryoscopic determination 1105 g/mol), and the reactor contents were heated to 50° C. A hydrogen content of 0.1% in the gas space of the reactor was set by metering in hydrogen and was later kept constant during the polymerization time by further metering in (online monitoring by gas chromatography). 18.5 mg of a rac-dimethylsilanediylbis(2,5,6-trimethyl-1-indenyl) zirconium dichloride, dissolved in 32 ml of a toluene solution of methylaluminoxane (corresponding to 50 mmol of Al), were then added to the reactor). The reactor was kept at 58° C. for 10 hours by cooling, the gases were released to a reactor pressure of 3 bar in order to remove the hydrogen, the reactor contents were then cooled to 45° C., 2.5 kg of ethylene were metered in, and the mixture was polymerized for a further 5 hours without further introduction of hydrogen. The polymerization was then terminated by means of CO$_2$ gas, and the polymer formed was separated from the suspension medium via a pressure filter and dried at 80° C./200 mbar for 24 hours. 17.5 kg of copolymer powder, corresponding to a mean metallocene activity of 63.1 kg of block copolymer/g of metallocene×h, were obtained.

VI=174 cm³/g; melting point=135° C., glass transition temperature −39° C.

The block copolymer contains 11.6% by weight of ethylene. Fractionation gave a content of 30.5% by weight of ethylene-propylene rubber.

EXAMPLE 16

The procedure was as in Example 10, but the metallocene used was 10.8 g of rac-dimethylsilanediylbis(2-methyl-5-phenyl-1-indenyl)zirconium dichloride. The activity of the metallocene was 139 kg of PP/g of metallocene×h.

VI=157 cm³/g; $M_w$=187,500 g/mol; $M_w/M_n$=2.0; melting point=139° C.

EXAMPLE 17

The procedure was as in Example 16, but the metallocene used was 15.4 mg of rac-dimethylsilanediylbis(2-methyl-6-phenyl-1-indenyl)zirconium dichloride. The activity of the metallocene was 69.5 kg of PP/g of metallocene×h.

VI=187 cm³/g; melting point 143° C.

We claim:

1. A process for the preparation of an olefin polymer by polymerization or copolymerization of an olefin of the formula $R^a$—CH=CH—$R^b$, in which $R^a$ and $R^b$ are identical or different and are a hydrogen atom or a hydrocarbon radical having 1 to 14 carbon atoms, or $R^a$ and $R^b$, together with the atoms connecting them, can form a ring, at a temperature of from −60° to 200° C., at a pressure of 0.5 to 100 bar, in solution, in suspension or in the gas phase, in the presence of a catalyst formed from a metallocene as transition-metal compound and a cocatalyst, wherein the metallocene is a compound of the formula I

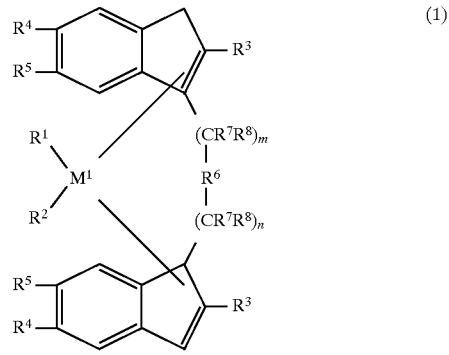

(1)

in which $M^1$ is a metal from group IVb, Vb or VIb of the Periodic Table, $R^1$ and $R^2$ are identical or different and are a hydrogen atom, a $C_1$–$C_{10}$-alkyl group, a $C_1$–$C_{10}$-alkoxy group, a $C_6$–$C_{10}$-aryl group, a $C_6$–$C_{10}$-aryloxy group, a $C_2$–$C_{10}$-alkenyl group, a $C_7$–$C_{40}$-arylalkyl group, a $C_7$–$C_{40}$-alkylaryl group, a $C_8$–$C_{40}$-arylalkenyl group or a halogen atom, $R^3$ is a $C_1$–$C_{20}$-alkyl group, a $C_6$–$C_{20}$-aryl group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, it also being possible for these radicals to be halogenated, $R^4$ and $R^5$ are identical or different and are a hydrogen atom, a $C_1$–$C_{20}$-alkyl group, a $C_6$–$C_{20}$-aryl group, a $C_2$–$C_{10}$-alkenyl group, a $C_7$–$C_{40}$-arylalkyl group, a $C_7$–$C_{40}$-alkylaryl group or a $C_8$–$C_{40}$-arylalkenyl group, it also being possible for these radicals to be halogenated, with the proviso that $R^4$ and $R^5$ both cannot simultaneously be hydrogen, $R^6$ is

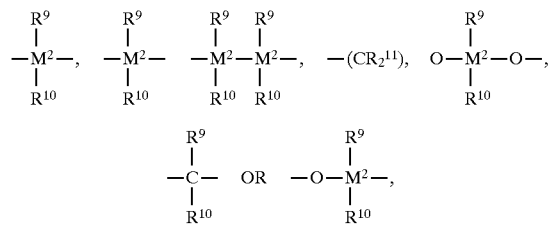

where $R^9$, $R^{10}$ and $R^{11}$ are identical or different and are a hydrogen atom, a halogen atom, a $C_1$–$C_{10}$-alkyl group, a $C_1$–$C_{10}$-fluoroalkyl group, a $C_6$–$C_{10}$-aryl group, a $C_6$–$C_{10}$-fluoroaryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group, or $R^9$ and $R^{10}$ or $R^9$ and $R^{11}$, in each case together with the atoms connecting them, form a ring, $M^2$ is silicon, germanium or tin, $R^7$ and $R^8$ are identical or different and are as defined for $R^9$, and m and n are identical or different and are zero, 1 or 2, where m plus n is zero, 1 or 2.

2. The process as claimed in claim 1, wherein, in the formula I, $M^1$ is Zr or Hf, $R^1$ and $R^2$ are identical or different and are ($C_1$–$C_3$)-alkyl or chlorine, $R^3$ and $R^4$ are identical or different and are ($C_1$–$C_{10}$)-alkyl, which may be halogenated, $R^5$ is hydrogen or ($C_1$–$C_{10}$)-alkyl, which may be halogenated, $R^6$ is a

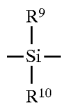

radical, and $R^9$ and $R^{10}$ are identical or different and are ($C_1$–$C_{10}$)-alkyl or ($C_6$–$C_{10}$)-aryl.

3. The process as claimed in claim 1, wherein the cocatalyst is an aluminoxane of the formula (II)

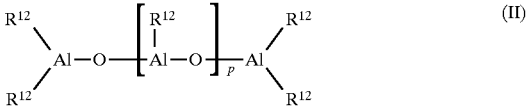

for the linear type and/or of the formula (III)

for the cyclic type, where, in the formulae (II) and (III), the radicals $R^{12}$ are identical or different and are a $C_1$–$C_6$-alkyl group, a $C_6$–$C_{18}$-aryl group, benzyl or hydrogen, and p is an integer from 2 to 50.

4. The process as claimed in claim 1, wherein the cocatalyst used is methylaluminoxane.

5. The process as claimed in claim 3, wherein the metallocene of the formula I is preactivated before use in the polymerization reaction by means of an aluminoxane of the formula II and/or III.

6. The process as claimed in claim 4, wherein, in the formula (I), $M^1$ is Zr or Hf, $R^1$ and $R^2$ are identical or different and are $(C_1-C_3)$-alkyl or chlorine, $R^3$ and $R^4$ are identical or different and are $(C_1-C_{10})$-alkyl, which may be halogenated, $R^5$ is hydrogen or $(C_1-C_{10})$-alkyl, which may be halogenated, $R^6$ is a

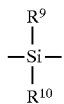

radical, and $R^9$ and $R^{10}$ are identical or different and are $(C_1-C_{10})$-alkyl or $(C_6-C_{10})$-aryl.

7. The process as claimed in claim 6, wherein $R^5$ is hydrogen.

8. A process as claimed in claim 1, wherein the metallocene is of formula I

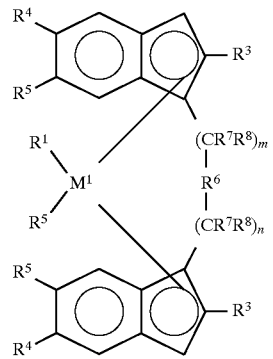

in which $M^1$ is a metal from group IVb of the Periodic Table, $R^1$ and $R^2$ are identical or different and are a hydrogen atom, a $C_1-C_{10}$-alkyl group, a $C_1-C_{10}$-alkoxy group, a $C_6-C_{10}$-aryl group, a $C_6-C_{10}$-aryloxy group, a $C_2-C_{10}$-alkenyl group, a $C_7-C_{40}$-arylalkyl group, a $C_7-C_{40}$-alkylaryl group, a $C_8-C_{40}$-arylalkenyl group or a halogen atom, $R^3$ and $R^4$ are identical or different and are $C_1-C_{10}$-alkyl, which is optionally halogenated, $R^5$ is hydrogen, $C_6-C_{10}$-aryl or $C_1-C_{10}$-alkyl, which is optionally halogenated, $R^9$ and $R^{10}$ are identical or different and are $C_1-C_{10}$-alkyl or $C_6-C_{10}$-aryl, $R^7$ and $R^8$ are identical or different and are as defined for $R^9$, and m and n are identical or different and are zero, 1 or 2, where m plus n is zero, 1 or 2.

9. The process as claimed in claim 4, wherein the metallocene is rac-dimethylsilanediylbis(2-methyl-5-isobutyl-1-indenyl)zirconium dichloride, rac-methylphenylsilanediylbis(2-methyl-5-isobutyl-1-indenyl)zirconium dichloride, rac-dimethylsilanediylbis(2-methyl-5-tert-butyl-1-indenyl)zirconium dichloride, rac-dimethylsilanediylbis(2,5,6-trimethyl-1-indenyl)zirconium dichloride, rac-dimethylsilanediylbis(2-methyl-5-phenyl-1-indenyl)zirconium dichloride or rac-dimethylsilanediylbis(2-methyl-6-phenyl-1-indenyl)zirconium dichloride.

10. The process as claimed in claim 2, wherein the cocatalyst used is methylaluminoxane and $M^1$ is Zr.

11. The process as claimed in claim 4, wherein the metallocene is rac-dimethylsilanediylbis(2-methyl-5-isobutyl-1-indenyl)zirconium dichloride.

12. The process as claimed in claim 8, wherein the cocatalyst used is methylaluminoxane and $M^1$ is Zr.

* * * * *